United States Patent [19]
Dubs et al.

[11] Patent Number: 5,356,976
[45] Date of Patent: Oct. 18, 1994

[54] 2,4-DIALKYL-6-SEC-ALKYLPHENOLS

[75] Inventors: Paul Dubs, Marly; Rita Pitteloud, Praroman, both of Switzerland

[73] Assignee: Ciba-Geigy Corporation, Ardsley, N.Y.

[21] Appl. No.: 90,836

[22] Filed: Jul. 12, 1993

[30] Foreign Application Priority Data

Jul. 15, 1992 [EP] European Pat. Off. ........ 92810538.6

[51] Int. Cl.$^5$ .......................... C07C 39/06; C08K 5/13
[52] U.S. Cl. .................................... 524/348; 524/349; 524/350; 568/743; 568/780; 568/781; 568/784; 568/785; 252/404; 252/482; 554/2
[58] Field of Search ............ 524/348, 349, 350; 568/743, 781, 784, 785, 780; 252/404, 48.2; 554/2

[56] References Cited

U.S. PATENT DOCUMENTS

| | | | |
|---|---|---|---|
| 2,581,907 | 1/1952 | Smith et al. | 524/350 |
| 3,183,273 | 5/1965 | Spacht . | |
| 3,394,020 | 7/1968 | Bell et al. | 568/784 |
| 3,424,717 | 1/1969 | Gottlieb et al. | 524/349 |
| 3,511,802 | 5/1970 | Newland et al. . | |
| 3,766,276 | 10/1973 | Goddard . | |
| 3,773,556 | 11/1973 | Rowland et al. | 524/349 |
| 3,776,276 | 10/1973 | Goddard | 568/747 |
| 3,933,927 | 1/1976 | Goddard | 568/784 |
| 4,071,565 | 1/1978 | Hollingshead | 524/349 |
| 5,098,945 | 3/1992 | Pitteloud et al. | 524/350 |

FOREIGN PATENT DOCUMENTS 0406169 6/1990 European Pat. Off. .
1396107 6/1975 United Kingdom .

OTHER PUBLICATIONS

C. A. 106:32349u (1987).
Abst. of Japan vol. 12 #286(M-727)(3133) Aug. 1988.
Abst of Japan vol. 2 #34(C-77)(4519) Mar. 1978.

Primary Examiner—Veronica P. Hoke
Attorney, Agent, or Firm—Luther A. R. Hall

[57] ABSTRACT

Compounds of formula I

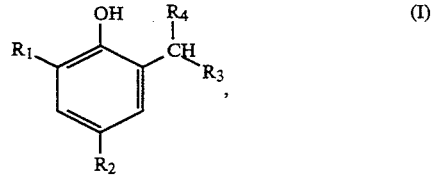

wherein $R_1$ is $C_1$–$C_4$n-alkyl, isopropyl, s-butyl, cyclopentyl, cyclohexyl or α-methylbenzyl, $R_2$ is $C_4$–$C_{18}$tert-alkyl or α,α-dimethylbenzyl, $R_3$ is $C_1$–$C_{28}$alkyl, and $R_4$ s methyl or ethyl, with the proviso that the —$CHR_3R_4$ group contains at least 4 carbon atoms, are suitable for stabilizing organic material which is susceptible to degradation induced by heat, oxidation or actinic light.

27 Claims, No Drawings

2,4-DIALKYL-6-SEC- ALKYLPHENOLS

The present invention relates to novel 2,4-dialkyl-sec-alkylphenols and to organic material stabilised therewith against degradation induced by heat, oxidation and actinic light.

A number of trialkylphenols, including 2,6-di-tert-butyl-4-methylphenol (®Swanox BHT), and the use thereof for stabilising organic material are known. The stabilisation of polypropylene resins with alkyl-substituted phenols, e.g. 2,6-bis(1-methylheptyl)-p-cresol, is disclosed in U.S. Pat. No. 3,511,802. Chemical Abstracts 106:32349u describes the use of sterically hindered phenols such as 2-sec-butyl-4,6-di-tert-butyl-phenol in stabiliser mixtures for separating by-products in the synthesis of 2-(2-chloroethoxy)ethanol. The use of sterically hindered phenols, for example 2,6-diisopropyl-4-octadecylphenol, as stabilisers for vinyl chloride resins is disclosed in Derwent Abstract 75900Y/43. British patent application 1 396 107 discloses 2,6-diisopropyl-4-tert-alkylphenols as educts for the preparation of 2,6-diisopropylphenol. U.S. Pat. No. 5,098,945 discloses 2,4-dimethyl-6-s-alkylphenols as stabilisers.

Specifically, the invention relates to compounds of formula I

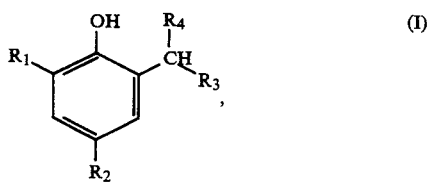

wherein
  $R_1$ is $C_1-C_4$n-alkyl, isopropyl, s-butyl, cyclopentyl, cyclohexyl or α-methylbenzyl,
  $R_2$ is $C_4-C_{18}$tert-alkyl or α,α-dimethylbenzyl,
  $R_3$ is $C_1-C_{28}$alkyl, and
  $R_4$ is methyl or ethyl, with the proviso that the —$CHR_3R_4$ group contains at least 4 carbon atoms.

$R_1$ defined as $C_1-C_4$n-alkyl is methyl, ethyl, n-propyl, and n-butyl. $R_1$ is preferably methyl, ethyl, s-butyl and cyclohexyl. Methyl is especially preferred. $R_2$ defined as $C_4-C_{18}$tert-alkyl will be taken to mean a —CXYZ radical, wherein X, Y and Z are each independently of one another $C_1-C_{15}$alkyl, and the sum of the number of carbon atoms in all 3 alkyl moieties (X+Y+Z) is 3 to 17. $R_2$ is thus typically tert-butyl, 2-methylbut-2-yl, 2-methylpent-2-yl, 2-methylhept-2-yl, 2-methylnon-2-yl, 2-methylundec-2-yl, 2-methylheptadec-2-yl, 3-methylpent-3-yl, 3-methylhept-3-yl, 3-methylnon-3-yl, 3-methylundec-3-yl, 3-methylheptadec-3-yl, and the like. The preferred meaning of $R_2$ is tert-butyl.

$R_3$ defined as $C_1-C_{28}$alkyl may be linear or branched and is typically methyl, ethyl, propyl, butyl, pentyl, hexyl, heptyl, octyl, nonyl, decyl, dodecyl, octadecyl, icosyl, docosyl, pentacosyl, hexacosyl or octacosyl. $R_3$ is preferably $C_1-C_{22}$alkyl, typically $C_8-C_{22}$alkyl, more particularly $C_{10}-C_{18}$alkyl and, most preferably, $C_{12}-C_{18}$alkyl. The preferred meaning of $R_3$ is linear alkyl.

$R_4$ is methyl or ethyl. Methyl is preferred.

The group —$CHR_3R_4$ contains 4 to 31, typically 6 to 31, preferably 10 to 25 and, most preferably 13 to 21, carbon atoms.

$R_1$ in preferred compounds of formula I is methyl, ethyl, s-butyl or cyclohexyl.

In further preferred compounds of formula I, $R_1$ is methyl or s-butyl, $R_2$ is $C_4-C_8$tert-alkyl and $R_3$ is $C_1-C_{22}$n-alkyl.

Compounds of formula I, wherein $R_1$ is methyl, are especially preferred.

Other preferred compounds of formula I are those wherein $R_4$ is methyl.

In other preferred compounds of formula I, $R_3$ is $C_8-C_{22}$n-alkyl.

In further interesting compounds of formula I, $R_2$ is $C_4-C_8$tert-alkyl, preferably tert-butyl.

Representative examples of compounds of formula I are:
4-t-butyl-2(1-methylundecyl)-6-methylphenol,
4-t-butyl-2(1-methyltridecyl)-6-methylphenol,
4-t-butyl-2(1-methylpentadecyl)-6-methylphenol,
4-t-butyl-2(1-methylheptadecyl)-6-methylphenol,
4-t-butyl-2(1-methylundecyl)-6-i-propylphenol,
4-t-butyl-2(1-methyltridecyl)-6-i-propylphenol,
4-t-butyl-2(1-methylpentadecyl)-6-i-propylphenol,
4-t-butyl-2(1-methylheptadecyl)-6-i-propylphenol,
6-s-butyl-4-t-butyl-2(1-methylundecyl)phenol,
6-s-butyl-4-t-butyl-2(1-methyltridecyl)phenol,
6-s-butyl-4-t-butyl-2(1-methylpentadecyl)phenol,
6-s-butyl-4-t-butyl-2(1-methylheptadecyl)phenol,
4-t-butyl-6-cyclohexyl-2(1-methylundecyl)phenol,
4-t-butyl-6-cyclohexyl-2(1-methyltridecyl)phenol,
4-t-butyl-6-cyclohexyl-2(1-methylpentadecyl)phenol,
4-t-butyl-6-cyclohexyl-2(1-methylheptadecyl)phenol,
4-t-butyl-2(1-methylundecyl)-6-α-methylbenzylphenol,
4-t-butyl-2(1-methyltridecyl)-6-α-methylbenzylphenol,
4-t-butyl-2(1-methylpentadecyl)-6-α-methylbenzylphenol,
4-t-butyl-2(1-methylheptadecyl)-6-α-methylbenzylphenol,
6-methyl-4-(1,1,3,3-tetramethylbutyl)-2(1-methylundecyl)phenol,
6-methyl-4-(1,1,3,3-tetramethylbutyl)-2(1-methyltridecyl)phenol,
6-methyl-4-(1,1,3,3-tetramethylbutyl)-2(1-methylpentadecyl)phenol,
6-methyl-4-(1,1,3,3-tetramethylbutyl)-2(1-methylheptadecyl)phenol,
6-isopropyl-4-(1,1,3,3-tetramethylbutyl)-2(1-methylundecyl)phenol ,
6-isopropyl-4-(1,1,3,3-tetramethylbutyl)-2(1-methyltridecyl)phenol,
6-isopropyl-4-(1,1,3,3-tetramethylbutyl)-2(1-methylpentadecyl)phenol,
6-isopropyl-4-(1,1,3,3-tetramethylbutyl)-2(1-methylheptadecyl)phenol,
6-s-butyl-4-(1,1,3,3-tetramethylbutyl)-2(1-methylundecyl)phenol,
6-s-butyl-4-(1,1,3,3-tetramethylbutyl)-2(1-methyltridecyl)phenol,
6-s-butyl-4-(1,1,3,3-tetramethylbutyl)-2(1-methylpentadecyl)phenol,
6-s-butyl-4-(1,1,3,3-tetramethylbutyl)-2(1-methylheptadecyl)phenol,
6-cyclohexyl-4-(1,1,3,3-tetramethylbutyl)-2(1-methylundecyl)phenol,
6-cyclohexyl-4-(1,1,3,3-tetramethylbutyl)-2(1-methyltridecyl)phenol,
6-cyclohexyl-4-(1,1,3,3-tetramethylbutyl)-2(1-methylpentadecyl)phenol,
6-cyclohexyl-4-(1,1,3,3-tetramethylbutyl)-2(1-methylheptadecyl)phenol, 6-α-methylbenzyl-4(1,1,3,3-tetramethylbutyl)-2(1-methylundecyl)phenol,
6-α-methylbenzyl-4(1,1,3,3-tetramethylbutyl)-2(1-methyltridecyl)phenol,
6-α-methylbenzyl-4(1,1,3,3-tetramethylbutyl)-2(1-methylpentadecyl)phenol,
6-α-methylbenzyl-4(1,1,3,3-tetramethylbutyl)-2(1-methylheptadecyl)phenol,
4(α,α-dimethylbenzyl)-2(1-methylundecyl)-6-methylphenol,
4(α,α-dimethylbenzyl)-2(1-methyltridecyl)-6-methylphenol,
4(α,α-dimethylbenzyl)-2(1-methylpentadecyl)-6-methylphenol,
4(α,α-dimethylbenzyl)-2(1-methylheptadecyl)-6-methylphenol,
4(α,α-dimethylbenzyl)-2(1-methylundecyl)-6-i-propylphenol,
4(α,α-dimethylbenzyl)-2(1-methyltridecyl)-6-i-propylphenol,
4(α,α-dimethylbenzyl)-2(1-methylpentadecyl)-6-i-propylphenol,
4(α,α-dimethylbenzyl)-2(1-methylheptadecyl)-6-i-propylphenol,
6-s-butyl-4(α,α-dimethylbenzyl)-2(1-methylundecyl)phenol,
6-s-butyl-4(α,α-dimethylbenzyl)-2(1-methyltridecyl)phenol,
6-s-butyl-4(α,α-dimethylbenzyl)-2(1-methylpentadecyl)phenol,
6-s-butyl-4(α,α-dimethylbenzyl)-2(1-methylheptadecyl)phenol,
6-cyclohexyl-4(α,α-dimethylbenzyl)-2(1-methylundecyl)phenol,
6-cyclohexyl-4(α,α-dimethylbenzyl)-2(1-methyltridecyl)phenol,
6-cyclohexyl-4(α,α-dimethylbenzyl)-2(1-methylpentadecyl)phenol,
6-cyclohexyl-4(α,α-dimethylbenzyl)-2(1-methylheptadecyl)phenol,
4(α,α-dimethylbenzyl)-6-α-methylbenzyl-2(1-methylundecyl)phenol,
4(α,α-dimethylbenzyl)-6-α-methylbenzyl-2(1-methyltridecyl)phenol,
4(α,α-dimethylbenzyl)-6-α-methylbenzyl-2(1-methylpentadecyl)phenol,
4(α,α-dimethylbenzyl)-6-α-methylbenzyl-2(1-methylheptadecyl)phenol.

The compounds of formula I can be prepared by methods analogous to known ones, conveniently by catalytic orthoalkylation of 2,4-dialkylphenols with α-olefins:

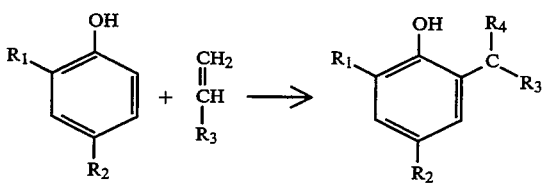

wherein $R_1$, $R_2$, $R_3$ and $R_4$ are as defined in claim 1. This process can be carried out in general accordance with the methods described in U.S. Pat. No. 3,766,276.

The reaction is expediently carried out in the temperature range from 80° to 250° C., preferably from 180° to 230° C., in the presence of a catalyst. Suitable catalysts are typically aluminium phenolates, preferably the aluminium phenolate of the corresponding phenol. It is also possible to use aluminium metal, alumina, aluminium alcoholates or trialkyl aluminium, in which case the corresponding aluminium phenolate is formed during the reaction. The catalyst is normally used in an amount of 1 to 10% molar.

The compounds of formula I can also be prepared by initially introducing the radical —$CR_3R_4$ into a 2-substituted phenol by orthoalkylation and then the substituent $R_2$ by subsequent paralkylation.

Suitable catalysts for the orthoalkylation step of this method are typically:

a) inorganic and organic acids such as sulfuric acid or p-toluenesulfonic acid;

b) zeoliths, e.g. ZSM zeolith;

c) acid clays, e.g. ®Fulmont 234, ®Fulcat 14 or ®Fulmont 700;

d) Friedel-Crafts catalysts, as described e.g. in Kozlikovski Ya. B. et al., Zh. Org. Khim. 23, 1918–24 (1987); Laan J. A. M.; Chem. Ind. 1, 34–35 (1987) and Kurashev M. V. et al.; Izv. Akad. Nauk. SSSR, Ser. Khim. 8, 1843–1846 (1986);

e) activated γ-alumina, as described e.g. in DE-B-1 142 873 and U.S. Pat. No. 3,367,981.

The particularly preferred catalyst for this reaction path is activated γ-alumina.

The second step, the paraalkylation, is carried out by methods commonly employed in the art, for example Friedel-Crafts alkylation.

Compounds of formula I, wherein $R_4$ is methyl, are mainly formed in the reaction of phenols with α-olefins. However, the formation of mixtures of compounds of formula I, wherein $R_4$ is methyl, with those compounds of formula I, wherein $R_4$ is ethyl, is also possible. The ratio of compounds of formula I in which $R_4$ is methyl to those in which $R_4$ is ethyl will depend mainly on the chosen route of synthesis as well as on the catalyst used. A mixture of compounds of formula I obtained from the synthesis can be separated conveniently by chromatographic methods, preferably gas chromatography and high-pressure liquid chromatography (HPLC). Normally it is not necessary to separate such mixtures. It is preferred to use the mixtures direct as stabilisers for organic material, as described below.

The invention also relates to mixtures of compounds of formula I, wherein $R_4$ is methyl, with those wherein $R_4$ is ethyl.

The weight ratio of the compounds of formula I, wherein $R_4$ is methyl, to those wherein $R_4$ is ethyl, is typically 99:1 to 1:99, preferably 99:1 to 90:10, most preferably 95:5 to 70:30.

Preferred mixtures are those in which the chain length of $R_3$ in compounds of formula I, wherein $R_4$ is methyl, is greater by one than in the compounds of formula I, wherein $R_4$ is ethyl. These are the mixtures which are able to form direct in the reaction of the phenols with the α-olefins. In this case, the substituent $R_3$ in the compounds in which R4 is methyl will necessarily contain one methylene group more than in the compounds in which $R_4$ is ethyl.

The phenols of formula I and mixtures thereof are admirably suitable for stabilising organic material which is sensitive to thermal, oxidative or actinic degradation. They are especially effective against oxidation- and heat-induced forms of degradation, in particular oxidation-induced degradation, of said material. They are therefore especially useful as excellent antioxidants.

The invention further relates to compositions comprising (a) an organic material which is susceptible to degradation induced by oxidation, heat or actinic light and (b) at least one compound of formula I or a mixture of such compounds as described hereinbefore.

Typical examples of such organic materials (a) are:

1. Polymers of monoolefins and diolefins, for example polypropylene, polyisobutylene, polybut-1-ene, poly-4-methylpent-1-ene, polyisoprene or polybutadiene, as well as polymers of cycloolefins, for instance of cyclopentene or norbornene, polyethylene (which optionally can be crosslinked), for example high density polyethylene (HDPE), low density polyethylene (LDPE), linear low density polyethylene (LLDPE), branched low density polyethylene (BLDPE).

Polyolefins, i.e. the polymers of monoolefins exemplified in the preceding paragraph, preferably polyethylene and polypropylene, can be prepared by different, and especially by the following, methods:

a) radical polymerisation (normally under high pressure and at elevated temperature).

b) catalytic polymerisation using a catalyst that normally contains one or more than one metal of groups Ivb, Vb, VIb or VIII of the Periodic Table. These metals usually have one or more than one ligand, typically oxides, halides, alcoholates, esters, ethers, amines, alkyls, alkenyls and/or aryls that may be either $\pi$- or $\sigma$-coordinated. These metal complexes may be in the free form or fixed on substrates, typically on activated magnesium chloride, titanium(III) chloride, alumina or silicon oxide. These catalysts may be soluble or insoluble in the polymerisation medium. The catalysts can be used by themselves in the polymerisation or further activators may be used, typically metal alkyls, metal hydrides, metal alkyl halides, metal alkyl oxides or metal alkyloxanes, said metals beeing elements of groups Ia, IIa and/or IIIa of the Periodic Table. The activators may be modified conveniently with further ester, ether, amine or silyl ether groups. These catalyst stystems are usually termed Phillips, Standard Oil Indiana, Ziegler (-Natta), TNZ (DuPont), metallocene or single site catalysts (SSC).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, for example ethylene/propylene copolymers, linear low density polyethylene (LLDPE) and mixtures thereof with low density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, propylene/butadiene copolymers, isobutylene/isoprene/-isoprene copolymers, ethylene-/alkyl acrylate copolymers, ethylene/alkyl methacrylate copolymers, ethylene/vinyl acetate copolymers and their copolymers with carbon monoxide or ethylene/acrylic acid copolymers and their salts (ionomers) as well as terpolymers of ethylene with propylene and a diene such as hexadiene, dicyclopentadiene or ethylidene-norbornene; and mixtures of such copolymers with one another and with polymers mentioned in 1) above, for example polypropylene/ethylene-propylene copolymers, LDPE/ethylene-vinyl acetate copolymers (EVA), LDPE/ethylene-acrylic acid copolymers (EAA), LLDPE/EVA, LLDPE/EAA and alternating or random polyalkylene/carbon monoxide copolymers and mixtures thereof with other polymers, for example polyamides.

4. Hydrocarbon resins (for example $C_5$–$C_9$) including hydrogenated modifications thereof (e.g. tackifiers) and mixtures of polyalkylenes and starch.

5. Polystyrene, poly(p-methylstyrene), poly($\alpha$-methylstyrene).

6. Copolymers of styrene or $\alpha$-methylstyrene with dienes or acrylic derivatives, for example styrene/butadiene, styrene/acrylonitrile, styrene/alkyl methacrylate, styrene/butadiene/alkyl acrylate, styrene/butadiene/alkyl methacrylate, styrene/maleic anhydride, styrene/acrylonitrile/methyl acrylate; mixtures of high impact strength of styrene copolymers and another polymer, for example a polyacrylate, a diene polymer or an ethylene/propylene/diene terpolymer; and block copolymers of styrene such as styrene/butadiene/styrene, styrene/isoprene/styrene, styrene/ethylene/butylene/styrene or styrene/ethylene/propylene/styrene.

7. Graft copolymers of styrene or $\alpha$-methylstyrene, for example styrene on polybutadiene, styrene on polybutadiene-styrene or polybutadiene-acrylonitrile copolymers; styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene; styrene and alkyl acrylates or methacrylates on polybutadiene; styrene and acrylonitrile on ethylene/propylene/diene terpolymers; styrene and acrylonitrile on polyalkyl acrylates or polyalkyl methacrylates, styrene and acrylonitrile on acrylate/butadiene copolymers, as well as mixtures thereof with the copolymers listed under 6), for example the copolymer mixtures known as ABS, MBS, ASA or AES polymers.

8. Halogen-containing polymers such as polychloroprene, chlorinated rubbers, chlorinated or sulfochlorinated polyethylene, copolymers of ethylene and chlorinated ethylene, epichlorohydrin homo- and copolymers, especially polymers of halogen-containing vinyl compounds, for example polyvinyl chloride, polyvinylidene chloride, polyvinyl fluoride, polyvinylidene fluoride, as well as copolymers thereof such as vinyl chloride/vinylidene chloride, vinyl chloride/vinyl acetate or vinylidene chloride/vinyl acetate copolymers.

9. Polymers derived from $\alpha,\beta$-unsaturated acids and derivatives thereof such as polyacrylates and polymethacrylates; polymethyl methacrylates, polyacrylamides and polyacrylonitriles, impact-modified with butyl acrylate.

10. Copolymers of the monomers mentioned under 9) with each other or with other unsaturated monomers, for example acrylonitrile/butadiene copolymers, acrylonitrile/alkyl acrylate copolymers, acrylonitrile/alkoxyalkyl acrylate or acrylonitrile/vinyl halide copolymers or acrylonitrile/alkyl methacrylate/butadiene terpolymers.

11. Polymers derived from unsaturated alcohols and amines or the acyl derivatives or acetals thereof, for example polyvinyl alcohol, polyvinyl acetate, polyvinyl stearate, polyvinyl benzoate, polyvinyl maleate, polyvinyl butyral, polyallyl phthalate or polyallyl melamine; as well as their copolymers with olefins mentioned in 1) above.

12. Homopolymers and copolymers of Cyclic ethers such as polyalkylene glycols, polyethylene oxide, polypropylene oxide or copolymers thereof with bisglycidyl ethers.

13. Polyacetals such as polyoxymethylene and those polyoxymethylenes which contain ethylene oxide as a comonomer, polyacetals modified with thermoplastic polyurethanes, acrylates or MBS.

14. Polyphenylene oxides and sulfides, and mixtures of polyphenylene oxides with styrene polymers or polyamides.

15. Polyurethanes derived from hydroxyl-terminated polyethers, polyesters or polybutadienes on the one hand and aliphatic or aromatic polyisocyanates on the other, as well as precursors thereof.

16. Polyamides and copolyamides derived from diamines and dicarboxylic acids and/or from aminocarboxylic acids or the corresponding lactams, for example polyamide 4, polyamide 6, polyamide 6/6, 6/10, 6/9, 6/12, 4/6, 12/12, polyamide 11, polyamide 12, aromatic polyamides starting from m-xylene diamine and adipic acid; polyamides prepared from hexamethylenediamine and isophthalic or/and terephthalic acid and with or without an elastomer as modifier, for example poly-2,4,4,-trimethylhexamethylene terephthalamide or poly-m-phenylene isophthalamide; and also block copolymers of the aforementioned polyamides with polyolefins, olefin copolymers, ionomers or chemically bonded or grafted elastomers; or with polyethers, e.g. with polyethylene glycol, polypropylene glycol or polytetramethylene glycol; as well as polyamides or copolyamides modified with EPDM or ABS; and polyamides condensed during processing (RIM polyamide systems).

17. Polyureas, polyimides, polyamide-imides and polybenzimidazoles.

18. Polyesters derived from dicarboxylic acids and diols and/or from hydroxycarboxylic acids or the corresponding lactones, for example polyethylene terephthalate, polybutylene terephthalate, poly-1,4-dimethylolcyclohexane terephthalate and polyhydroxybenzoates, as well as block copolyether esters derived from hydroxyl-terminated polyethers; and also polyesters modified with polycarbonates or MBS.

19. Polycarbonates and polyester carbonates.

20. Polysulfones, polyether sulfones and polyether ketones.

21. Crosslinked polymers derived from aldehydes on the one hand and phenols, ureas and melamines on the other hand, such as phenol/formaldehyde resins, urea/-formaldehyde resins and melamine/formaldehyde resins.

22. Drying and non-drying alkyd resins.

23. Unsaturated polyester resins derived from copolyesters of saturated and unsaturated dicarboxylic acids with polyhydric alcohols and vinyl compounds as crosslinking agents, and also halogen-containing modifications thereof of low flammability.

24. Crosslinkable acrylic resins derived from substituted acrylates, for example epoxy acrylates, urethane acrylates or polyester acrylates.

25. Alkyd resins, polyester resins and acrylate resins crosslinked with melamine resins, urea resins, polyisocyanates or epoxy resins.

26. Crosslinked epoxy resins derived from polyepoxides, for example from bisglycidyl ethers or from cycloaliphatic diepoxides.

27. Natural polymers such as cellulose, rubber, gelatin and chemically modified homologous derivatives thereof, for example cellulose acetates, cellulose propionates and cellulose burytates, or the cellulose ethers such as methyl cellulose; as well as rosins and their derivatives.

28. Blends of the aforementioned polymers (polyblends), for example PP/EPDM, Polyamide/EPDM or ABS, PVC/EVA, PVC/ABS, PVC/MBS, PC/ABS, PBTP/ABS, PC/ASA, PC/BT, PVC/CPE, PVC/acrylates, POM/thermoplastic PUR, PC/thermoplastic PUR, POM/acrylate, POM/MBS, PPO/HIPS, PPO/PA 6.6 and copolymers, PA/HDPE, PA/PP, PA/PPO.

In preferred compositions, component (a) is a polystyrene, a substituted polystyrene, a co- or terpolymer of polystyrene or substituted polystyrene. Examples will be found especially in items 6 and 7 of the above list Component (a) is preferably selected from the group consisting of impact-resistant polystyrene (IPS), styrene-acrylonitrile copolymers (SAN) and acrylonitrile-butadiene-styrene terpolymers (ABS), preferably acrylonitrile-butadiene-styrene polymers (ABS) and methyl methacrylate-butadiene-styrene graft copolymers (MBS).

Also useful as component (a) are organic materials selected from the group consisting of polycarbonate, polyester carbonate, polyurethane, polyamide, copolyamide, polyacetal and polyphenylene oxide. Suitable examples will be found in items 13, 15 and 16 of the above list.

Preferred compositions are also those wherein component (a) is a polyolefin. Examples will be found in particular in items 1–3 of the above list. Polyethylene and polypropylene are of particular interest.

The novel compositions conveniently contain 0.01 to 10%, preferably 0.05 to 5%, most preferably 0.1 to 2% of at least one compound of formula I or of a mixture of compounds of formula I, wherein $R_4$=methyl, with those compounds of formula I, wherein $R_4$=ethyl, based on the total weight of the organic material to be stabilised.

Besides the compounds of formula I, the novel compositions may also contain additional conventional additives, for example:

1. Antioxidants 1.1. Alkylated monophenols, for example 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(αmethylcyclohexyl)-4,6-dimethylphenol, 2,6-dioctadecyl-4-methylphenol, 2,4,6-tricyclohexylphenol, 2,6-di-tert-butyl-4-methoxymethylphenol, 2,6-di-nonyl-4-methylphenol, 2,4dimethyl-6-(1'-methylundec-1'-yl)phenol, 2,4-dimethyl-6-(1'-methylheptadec-1'-yl)phenol, 2,4-dimethyl-6-(1'-methyltridec-1'-yl)phenol and mixtures therof.

1.2. Alkylthiomethylphenols, for example 2,4-dioctylthiomethyl-6-tert-butylphenol, 2,4-dioctylthiomethyl-6-methylphenol, 2,4-dioctylthiomethyl-6-ethylphenol, 2,6-di-do-decylthiomethyl-4-nonylphenol.

1.3. Hydroquinones and alkylated hydroquinones, for example 2,6-di-tert-butyl-4-methoxyphenol, 2,5-ditert-butylhydroquinone, 2,5-di-tert-amylhydroquinone, 2,6-diphenyl-4-octadecyloxyphenol, 2,6-di-tert-butylhydroquinone, 2,5-di-tert-butyl4-hydroxyanisole, 3,5-di-tert-butyl-4-hydroxyanisole, 3,5-di-tert-butyl-4-hydroxyphenylstearate, bis-(3,5-di-tert-butyl-4-hydroxyphenyl)adipate.

1.4. Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 4,4'-thiobis-(3,6-di-sec-amylphenol), 4,4'-bis-(2,6-dimethyl-4-hydroxyphenyl)disulfide.

1.5. Alkylidenebisphenols, for example 2,2'-methylenebis(6-tert-butyl-4-methylphenol), 2,2'-methylenebis(6-tert-butyl-4-ethylphenol), 2,2'-methylenebis[4-methyl-6-(α-methylcyclohexyl)-phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-(α-methylbenzyl)-4-nonylphenol], 2,2'-methylenebis[6-(α,α-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2methylphenyl)butane, 1,1-bis(5-tert-butyl-4-hydroxy-2-methyl-phenyl)-3-n-dodecylmercaptobutane, ethylene glycol bis[3,3-bis(3'-tert-butyl-4'-hydroxyphenyl)butyrate], bis(3-tert-butyl-4-hydroxy-5-methyl-phenyl)dicyclopentadiene, bis[2-(3'-tert-butyl-2'-hydroxy-5'-methylbenzyl)-6-tert-butyl-4-methylphenyl]terephthalate, 1,1-bis-(3,5-dimethyl-2-hydroxyphenyl)butane, 2,2-bis-(3,5-di-tert-butyl-4-hydroxyphenyl)propane, 2,2-bis-(5-tert-butyl-4-hydroxy2-methylphenyl)-4-n-dodecylmercaptobutane, 1,1,5,5-tetra-(5-tert-butyl-4-hydroxy2-methylphenyl)pentane.

1.6. O-, N- and S-benzyl compounds, for example 3,5,3',5'-tetra-tert-butyl-4,4'-dihydroxydibenzyl ether, octadecyl-4-hydroxy-3,5-dimethylbenzylmercaptoacetate, tris-(3,5-di-tert-butyl-4-hydroxybenzyl)amine, bis(4-tert-butyl-3-hydroxy-2,6-dimethylbenzyl)dithioterephthalate, bis(3,5-di-tert-butyl-4-hydroxybenzyl)sulfide, isooctyl-3,5di-tert-butyl-4-hydroxybenzylmercaptoacetate.

1.7. Hydroxybenzylated malonates, for example dioctadecyl-2,2-bis-(3,5-di-tert-butyl-2-hydroxybenzyl)-malonate, di-octadecyl-2-(3-tert-butyl-4-hydroxy-5-methylbenzyl)-malonate, di-dodecylmercaptoethyl-2,2-bis-(3,5-di-tert-butyl-4-hydroxybenzyl)malonate, bis[4-(1,1,3,3-tetramethylbutyl)-phenyl]-2,2-bis(3,5-di-tert-butyl-4-hydroxybenzyl)-malonate.

1.8. Aromatic hydroxybenzyl compounds, for example 1,3,5-tris-(3,5-di-tert-butyl-4-hydroxybenzyl)-2,4,6-trimethylbenzene, 1,4-bis(3,5-di-tert-butyl-4-hydroxybenzyl)-2,3,5,6-tetramethylbenzene, 2,4,6-tris(3,5-di-tert-butyl-4-hydroxybenzyl)phenol.

1.9. Triazine Compounds, for example 2,4-bis(octylmercapto)-6-(3,5-di-tert-butyl-4-hydroxyanilino)-1,3,5-triazine, 2-octylmercapto-4,6-bis(3,5-di-tert-butyl-4-hydroxyanilino)-1,3,5-triazine, 2-octylmercapto-4,6-bis(3,5-di-tert-butyl-4-hydroxyphenoxy)-1,3,5-triazine, 2,4,6-tris(3,5-di-tert-butyl-4-hydroxyphenoxy)-1,2,3-triazine, 1,3,5-tris(3,5-di-tert-butyl-4-hydroxybenzyl)isocyanurate, 1,3,5-tris(4-tert-butyl-3-hydroxy-2,6-dimethylbenzyl)isocyanurate, 2,4,6-tris(3,5-di-tert-butyl-4-hydroxyphenylethyl)-1,3,5-triazine, 1,3,5-tris(3,5-di-tert-butyl-4-hydroxyphenylpropionyl)-hexahydro-1,3,5-triazine, 1,3,5-tris(3,5-dicyclohexyl-4-hydroxybenzyl)isocyanurate.

1.10. Benzylphosphonates, for example dimethyl-2,5-di-tert-butyl-4-hydroxybenzylphosphonate, diethyl-3,5-di-tert-butyl-4-hydroxybenzylphosphonate, dioctadecyl3,5-di-tert-butyl-4-hydroxybenzylphosphonate, dioctadecyl-5-tert-butyl-4-hydroxy3-methylbenzylphosphonate, the calcium salt of the monoethyl ester of 3,5-di-tert-butyl-4-hydroxybenzylphosphonic acid.

1.11. Acylaminophenols, for example 4-hydroxylauranilide, 4-hydroxystearanilide, octyl N-(3,5-di-tert-butyl-4-hydroxyphenyl)carbamate.

1.12. Esters of β-(3,5-di-tert-butyl-4-hydroxyphenyl)-propionic acid with mono- or polyhydric alcohols, e.g. with methanol, ethanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.13. Esters of β-(5-tert-butyl-4-hydroxy-3-methylphenyl)propionic acid with mono- or polyhydric alcohols, e.g. with methanol, ethanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.14 Esters of 62-(3,5-dicyclohexyl4-hydroxyphenyl)-propionic acid with mono- or polyhydric alcohols, e.g. with methanol, ethanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.15 Esters of 3,5-di-tert.-butyl-4-hydroxyphenyl acetic acid with mono-or polyhydric alcohols, e.g. with methanol, ethanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.16. Amides of β-(3,5-di-tert-butyl-4-hydroxyphenyl)propionic acid e.g. N,N'-bis(3,5-di-tert-butyl-4-hydroxyphenylpropionyl)hexamethylenediamine, N,N'-bis(3,5-di-tert-butyl-4-hydroxyphenylpropionyl)trimethylenediamine, N,N'-bis(3,5-di-tert-butyl-4-hydroxyphenylpropionyl)hydrazine.

2. UV absorbers and light stabilisers 2.1. 2-(2'-Hydroxyphenyl)benzotriazoles, for example 2-(2'-hydroxy-5'-methylphenyl)benzotriazole, 2-(3',5'-di-tert-butyl-2'-hydroxyphenyl)benzotriazole, 2-(5'-tert-butyl-2'-hydroxyphenyl)benzotriazole, 2-(2'-hydroxy-5'-(1,1,3,3-tetramethylbutyl)phenyl)benzotriazole, 2-(3',5'-di-tert-butyl-2'-hydroxyphenyl)-5-chlorobenzotriazole, 2-(3'-tert-butyl-2'-hydroxy-5'-methylphenyl)-5-chlorobenzotriazole, 2-(3'-sec-butyl-5'-tert-butyl-2'-hydroxyphenyl)benzotriazole, 2-(2'-hydroxy-4'-octyloxyphenyl)benzotriazole, 2-(3',5'-di-tert-amyl-2'-hydroxyphenyl)benzotriazole, 2-(3',5'-bis-(α,α-dimethylbenzyl)-2'-hydroxyphenyl)benzotriazole, mixture of 2-(3'-tert-butyl-2'-hydroxy-5'-(2-octyloxycarbonylethyl)phenyl)-5-chlorobenzotriazole, 2-(3'-tert-butyl-5'-[2-(2-ethylhexoxy)-carbonylethyl]-2'-hydroxyphenyl)-5-chlorobenzotriazole, 2-(3'-tert-butyl-2'-hydroxy-5'-(2-methoxycarbonylethyl)phenyl)-5-chlorobenzotriazole, 2-(3'-tert-butyl-2'-hydroxy-5'-(2-methoxycarbonylethyl)phenyl)benzotriazole, 2-(3'-tert-butyl-2'-hydroxy-5'-(2-octyloxycarbonylethyl)phenyl)-benzotriazole, 2-(3'-tert-butyl-5'-[2-(2-ethylhexoxy)-carbonylethyl]-2'-hydroxyphenyl)benzotriazole, 2-(3'-dodecyl-2'-hydroxy-5'-methylphenyl)benzotriazole, and 2-(3'-tert-butyl-2'-hydroxy-5'-(2-isoctyloxycarbonylethyl)phenylbenzotriazole, 2,2'-methylene-bis[4-(1,1,3,3-tetramethylbutyl)-6-benzotriazole-2-ylphenol]; the transesterification product of 2-[3'-tert-butyl-5'-(2-methoxycarbonylethyl)-2'-hydroxyphenyl]-2H-benzotriazole with polyethylene glycol 300; [R—CH2CH2—COO(CH2)3]2, where R=3'-tert-butyl-4'-hydroxy-5'-2H-benzotriazol-2-ylphenyl.

2.2. 2-Hydroxybenzophenones, for example the 4-hydroxy, 4-methoxy, 4-octyloxy, 4-decyloxy, 4-dodecyloxy, 4-benzyloxy, 4,2',4'-trihydroxy and 2'-hydroxy-4,4'-dimethoxy derivatives.

2.3. Esters of substituted and unsubstituted benzoic acids, as for example 4-tertbutylphenyl salicylate, phenyl salicylate, octylphenyl salicylate, dibenzoyl resorcinol, bis(4-tert-butylbenzoyl) resorcinol, benzoyl resorcinol, 2,4-di-tertbutylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, 2-methyl-4,6-di-tert-butylphenyl 3,5-di-tert-butyl-4-hydroxybenzoate.

2.4. Acrylates, for example ethyl α-cyano-β,β-diphenylacrylate, isoctyl α-cyano-β,β-di-phenylacrylate, methyl α-carbomethoxycinnamate, methyl α-cyano-β-methyl-p-methoxycinnamate, butyl α-cyano-β-methyl-p-methoxy-cinnamate, methyl α-carbomethoxy-p-methoxycinnamate and N-(β-carbomethoxy-β-cyanovinyl)-2-methylindoline.

2.5. Nickel compounds, for example nickel complexes of 2,2'-thio-bis-[4-(1,1,3,3-tetramethylbutyl)-phenol], such as the 1:1 or 1:2 complex, with or without additional ligands such as n-butylamine, triethanolamine or N-cyclohexyldiethanolamine, nickel dibutyldithiocarbamate, nickel salts of the monoalkyl esters, e.g. the methyl or ethyl ester, of 4-hydroxy-3,5-di-tert-butylbenzylphosphonic acid, nickel complexes of ketoximes, e.g. of 2-hydroxy-4-methylphenyl undecylketoxime, nickel complexes of 1-phenyl-4-lauroyl-5-hydroxypyrazole, with or without additional ligands.

2.6. Sterically hindered amines, for example bis(2,2,6,6-tetramethyl-piperidyl)sebacate, bis(2,2,6,6-tetramethyl-piperidyl)succinate, bis(1,2,2,6,6-pentamethylpiperidyl)sebacate, bis(1,2,2,6,6-pentamethylpiperidyl) n-butyl-3,5-di-tert-butyl-4-hydroxybenzylmalonate, the condensate of 1-(2-hydroxyethyl)-2,2,6,6-tetramethyl-4-hydroxypiperidine and succinic acid, the condensate of N,N'-bis(2,2,6,6-tetramethyl-4-piperidyl)-hexamethylenediamine and 4-tert-octylamino-2,6-dichloro-1,3,5-triazine, tris(2,2,6,6-tetramethyl-4-piperidyl) nitrilotriacetate, tetrakis(2,2,6,6-tetramethyl-4-piperidyl)-1,2,3,4-butane-tetracarboxylate, 1,1'-(1,2-ethanediyl)bis(3,3,5,5-tetramethylpiperazinone), 4-benzoyl-2,2,6,6-tetramethylpiperidine, 4-stearyloxy-2,2,6,6-tetrarnethylpiperidine, bis(1,2,2,6,6-pentamethylpiperidyl)-2-n-butyl-2-(2-hydroxy-3,5-di-tert-butylbenzyl)malonate, 3-n-octyl-7,7,9,9-tetramethyl-1,3,8-triazasprio[4.5]decan-2,4-dion, bis(1-octyloxy-2,2,6,6-tetramethylpiperidyl)sebacate, bis(1-octyloxy-2,2,6,6-tetramethylpiperidyl)succinate, the condensate of N,N'-bis-(2,2,6,6-tetramethyl-4-piperidyl)hexamethylenediamine and 4-morpholino-2,6-dichloro-1,3,5-triazine, the condensate of 2-chloro-4,6-bis(4-n-butylamino-2,2,6,6-tetramethylpiperidyl)-1,3,5-triazine and 1,2-bis(3-aminopropylamino)ethane, the condensate of 2-chloro-4,6-di-(4-n-butylamino-1,2,2,6,6-pentamethylpiperidyl)-1,3,5-triazine and 1,2-bis-(3-aminopropylamino)ethane, 8-acetyl-3-dodecyl-7,7,9,9-tetramethyl-1,3,8-triazaspiro[4.5]-decane-2,4-dione, 3-dodecyl-1-(2,2,6,6-tetramethyl-4-piperidyl)pyrrolidine-2,5-dione, 3-dodecyl-1-(1,2,2,6,6-pentamethyl-4-piperidyl)pyrrolidine-2,5-dione.

2.7. Oxamides, for example 4,4'-dioctyloxyoxanilide, 2,2'-dioctyloxy-5,5'-di-tert-butoxanilide, 2,2'-didodecyloxy-5,5'-di-tert-butoxanilide, 2-ethoxy-2'-ethoxanilide, N,N'-bis(3-dimethylaminopropyl)oxamide, 2ethoxy-5-tert-butyl-2'-ethoxanilide and its mixture with 2-ethoxy-2'-ethyl-5,4'-di-tert-butoxanilide and mixtures of ortho- and paramethoxy-disubstituted oxanilides and mixtures of o- and p-ethoxy-disubstituted oxanilides.

2.8. 2-(2-Hydroxyphenyl)-1,3,5-triazines, for example 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine, 2-[2-hydroxy-4-(2hydroxy-3-butyloxy-propoxy)-phenyl]-4,6-bis(2,4-dimethyl)-1,3,5-triazine, 2-[2-hydroxy-4-(2-hydroxy-3-octyloxy-propyloxy)-phenyl]-4,6-bis(2,4-dimethyl)-1,3,5-triazine.

3. Metal deactivators, for example N,N'-diphenyloxamide, N-salicylal-N'-salicyloyl hydrazine, N,N'-bis(salicyloyl) hydrazine, N,N'-bis(3,5-di-tert-butyl-4-hydroxyphenylpropionyl) hydrazine, 3-salicyloylamino-1,2,4-triazole, bis(benzylidene)oxalyl dihydrazide, oxanilide, isophthaloyl dihydrazide, sebacoyl bisphenylhydrazide, N,N'-diacetaladipoyl dihydrazide, N,N'-bis(salicyloyl- )oxalyl dihydrazide, N,N'-bis(salicyloyl)thiopropionyl dihydrazide.

4. Further phosphites and phosphonites, for example triphenyl phosphite, diphenyl alkyl phosphites, phenyl dialkyl phosphites, tris(nonylphenyl) phosphite, trilauryl phosphite, trioctadecyl phosphite, distearyl pentaerythritol diphosphite, tris(2,4-di-tert-butylphenyl) phosphite, diisodecyl pentaerythritol diphosphite, bis(2,4-di-tert-butylphenyl) pentaerythritol diphosphite, bis(2,6-di-tert-butyl-4-methylphenyl)-pentaeryt hritol diphosphite, diisodecyloxypentaerythritol diphosphite, bis(2,4-di-tert-butyl-6-methylphenyl)pentaerythritol diphosphite, bis(2,4,6-tris(tert-butylphenyl)pentaerythritol diphsophite, tristearyl sorbitol triphosphite, tetrakis(2,4-di-tert-butylphenyl) 4,4'-biphenylene diphosphonite, 6-isooctyloxy-2,4,8,10-tetra-tert-butyl-12H-dibenz[d,g]-1,3,2-dioxaphosphocin, 6-fluoro-2,4,8,10-tetra-tert-butyl-12-methyl-dibenz[d,g]-1,3,2-dioxaphosphocin, bis(2,4-di-tert-butyl-6-methylphenyl)methylphosphite, bis(2,4-di-tert-butyl-6-methylphenyl)ethylphosphite.

5. Peroxide scavengers, for example esters of β-thiodipropionic acid, for example the lauryl, stearyl, myristyl or tridecyl esters, mercaptobenzimidazole or the zinc salt of 2-mercaptobenzimidazole, zinc dibutyldithiocarbamate, diotadecyl disulfide, pentaerythritol tetrakis(β-dodecylmercapto)propionate.

6. Polyamide stabilisers, for example copper salts in combination with iodides and/or phosphorus compounds and salts of divalent manganese.

7. Basic co-stabilisers, for example melamine, polyvinylpyrrolidone, dicyandiamide, triallyl cyanurate, urea derivatives, hydrazine derivatives, mines, polyamides, polyurethanes, alkali metal salts and alkaline earth metal salts of higher fatty acids for example calcium stearate, zinc stearate, magnesium behenate, magnesium stearate, sodium ricinoleate and potassium palmitate, antimony pyrocatecholate or zinc pyrocatecholate.

8. Nucleating agents, for example 4-tert-butylbenzoic acid, adipic acid, diphenylacetic acid.

9. Fillers and reinforcing agents, for example calcium carbonate, silicates, glass fibres, asbestos, talc, kaolin, mica, barium sulfate, metal oxides and hydroxydes, carbon black, graphite.

10. Other additives, for example plasticisers, lubricants, emulsifiers, pigments, optical brighteners, flame-proofing agents, antistatic agents and blowing agents.

11. Benzofuranones and indolinones, for example those disclosed in U.S. Pat. No 4,325,863 or U.S. Pat No. 4,338,244.

The invention further relates to the use of compounds of formula I, or of the above described mixtures of compounds of formula I or of products which are obtained by reacting a phenol with an α-olefin, for stabilising organic material that is susceptible to degradation induced by heat, oxidation or actinic light.

The invention also relates to a process for stabilising organic material that is susceptible to degradation induced by heat, oxidation or actinic light, which comprises incorporating in or applying to said material at least one compound of formula I, one of the above described mixtures of compounds of formula I or one product which is obtained by reacting a phenol with an α-olefin.

Incorporation of the compounds of formula I or mixtures thereof, as well as further additives, in the organic material is effected by methods known in the art, conveniently before or during shaping, or also by applying a solution or dispersion of the compound to the organic material, with subsequent evaporation of the solvent. The compounds of formula I may also be added in the form of a masterbatch which contains the compounds to the material to be stabilised, typically in a concentration of 2.5 to 25% by weight.

The novel compounds can be added before or during polymerisation or before crosslinking.

The novel compounds can be incorporated in the material to be stabilised in pure form, as solutions or dispersions, or encapsulated in waxes, oils or polymers.

The stabilised materials so obtained can be used in a wide range of forms, typically as sheets, filaments, ribbons, moulded articles, profiles, or as binders for paints and varnishes, adhesives or putties.

The novel compounds may also be suitably used as chain terminators in the anionic polymerisation of 1,3-dienes.

The invention is illustrated in more detail by the following Examples in which, and also in the remainder of the description and in the claims, parts and percentages are by weight, unless otherwise stated.

EXAMPLE 1

Preparation of 4-tert-butyl-2-(1-methylpentadecyl)-6-methylphenol

A 2.5 l sulfonation flask is charged with a mixture of 619 g (3.8 mol) of 4-tert-butyl-2-methylphenol, 896 g (4 mol) of linear α-hexadecene and 38.5 g of aluminium tris(4-tert-butyl-2-methylphenolate) as catalyst, and heated to 215° C. for 6–8 hours. The reaction mixture is then cooled to 70° C., 30 ml of a 32% solution of ammonia are added and the batch is stirred for 30 minutes at 70° C. The precipitated aluminium hydroxide is separated by filtration. Distillation of the liquid residue under a high vacuum (190°–210° C./0.001 mbar) gives 1.13 kg (77% of theory) of 4-tert-butyl-2-(1-methylpentadecyl)-6-methylphenol as a colourless liquid.

Elemental analysis:

| Elemental analysis: | | | | | |
|---|---|---|---|---|---|
| calcd | C: | 83.44% | found: | C: | 83,47% |
| | H: | 12.45% | | H: | 12.66% |

EXAMPLES 2–10

The compounds of Examples 2–10 are prepared in accordance with the general procedure for obtaining the compound of Example 1, using the corresponding phenols and α-olefins as starting materials. Their structures and physical data are indicated in the Table.

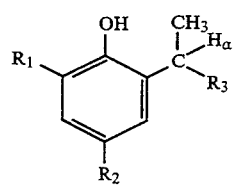

TABLE 1

| Ex. | R$_1$ | R$_2$ | R$_3$ | C % calcd | C % found | H % calcd | H % found | $^1$H-NMR (300 MHz) H$_\alpha$ (δ ppm) |
|---|---|---|---|---|---|---|---|---|
| 2 | CH$_3$ | t-C$_8$H$_{17}$* | n-C$_{14}$H$_{29}$ | 83.71 | 83.74 | 12.69 | 12.65 | 2.985 (sextuplet; J = 7.1 Hz) |
| 3 | CH$_3$ | t-C$_4$H$_9$ | n-C$_{12}$H$_{25}$ | 83.26 | 83.34 | 12.30 | 12.48 | 2.981 (sextuplet; J = 6.987 Hz) |
| 4 | CH$_3$ | t-C$_4$H$_9$ | n-C$_{10}$H$_{21}$ | 83.07 | 83.15 | 12.12 | 12.18 | 2.982 (sextuplet; J = 6.969 Hz) |
| 5 | CH$_3$ | t-C$_4$H$_9$ | n-C$_{16}$H$_{33}$ | 83.58 | 83.51 | 12.58 | 12.98 | 2.979 (sextuplet; J = 6.99 Hz) |
| 6 | CH$_3$ | t-C$_4$H$_9$ | n-C$_6$H$_{13}$ | 82.55 | 82.76 | 11.67 | 11.79 | 2.982 (sextuplet; J = 6.999 Hz) |
| 7 | CH$_3$ | t-C$_5$H$_{11}$*$^1$ | n-C$_{14}$H$_{29}$ | 83.51 | 83.6 | 12.52 | 12.73 | 2.979 (sextuplet; J = 6.63 Hz) |
| 8 | s-C$_4$H$_9$ | t-C$_4$H$_9$ | n-C$_{14}$H$_{29}$ | 83.65 | 83.74 | 12.64 | 12.67 | 2.875 (sextuplet; J = 6.87 Hz) |
| 9 | CH$_3$ | t-C$_4$H$_9$ | n-C$_{18}$H$_{37}$ — n-C$_{22}$H$_{45}$*$^2$ | 83.83 | 83.74 | 12.79 | 13.09 | 2.978 (sextuplet; J = 6.996 Hz) |
| 10 | CH$_3$ | t-C$_4$H$_9$ | n-C$_{12}$H$_{25}$ — n-C$_{16}$H$_{31}$*$^3$ | 83.44 | 83.20 | 12.5 | 12.45 | 2.978 (sextuplet; J = 7.02 Hz) |

*: t-C$_8$H$_{17}$ is 2-methylhept-2-yl
*$^1$: t-C$_5$H$_{11}$ is 2-methylbut-2-yl
*$^2$: a mixture of α-olefins with C$_{18}$, C$_{20}$ and C$_{22}$ in the ratio 1:1:1 was used
*$^3$: a mixture of α-olefins with C$_{12}$, C$_{14}$ and C$_{16}$ in the ratio 1:1:1 was used

EXAMPLE 11

Stabilisation of Acrylonitrile-Butadiene-Styrene Terpolymer (ABS)

The additives listed in Table 2 are dissolved in 40 ml of a mixture of hexane/isopropanol. With efficient stirring, the solution is added to a dispersion of 100 g of ABS in 600 g of water and the solution is completely absorbed by the ABS in a short time (c. 1 minute). The ABS powder is collected by suction filtration and vacuum dried at 40° C. for 40 hours. To the dry powder are then added 2% of titanium dioxide (pigment) and 1% of ethylene bis(stearamide) (lubricant). The mixture is then compounded for 4 minutes on a two-roll mill at 180° C.

The rolled sheet is compressed at 175° C. to a 0.88 mm sheet from which test specimens measuring 45×17 mm$^2$ are punched. The effectiveness of the additives incorporated in the polymer is tested by heat ageing in a recirculating air oven at 180° C. The colour development after 45 minutes is the criterion for assessing the effectiveness of the additives. The colour intensity is measured by the Yellowness Index of ASTM D 1925-70. Higher values denote more intensive yellowing. The tests show that yellowing is effectively inhibited by the novel compounds incorporated in the polymer.

TABLE 2

| Additive | Yellowness Index after 45 min at 180° C. |
|---|---|
| — | 78 |
| 0.5% DLTDP | 75 |
| 0.5% DLTDP + 0.25% of the compound of Example | |
| 1 | 30 |
| 2 | 30 |
| 3 | 30 |
| 4 | 30 |
| 5 | 28 |
| 6 | 30 |
| 7 | 29 |
| 8 | 29 |
| 9 | 30 |
| 10 | 31 |

DLTDP = dilaurylthiodipropionate

EXAMPLE 12

Stabilisation of Polypropylene 100 parts of the polymer ®Statoil MF 4 (polypropylene sold by Petrokjemi Statoil, Norway; MF[230° C./2.16 kg] 4.3), 0.10% of the phenol of Example 1 and 0.05% of calcium stearate are kneaded in a Brabender plastograph for 10 minutes at 200° C. and 50 rpm.

The mixture is then compressed at 200° C. for 6 minutes to 2 mm sheets from which discs of 26 mm diameter are punched as test specimens.

The Yellowness Index of these test specimens is then determined (photometer: Datacolor 3890, aperture 27, without UV, without gloss, standard light C., 2° detector). The results are reported in Table 3.

EXAMPLE 13

Stabilisation of High-Density Polyethylene 100 parts of ®Statoil H 870 (high density polyethylene sold by Petrokjemi Statoil, Norway; MF[190° C./5.0 kg] 2.9), 0.10% of the phenol of Example 1 and 0.05% of calcium stearate are kneaded in a Brabender plastograph for 10 minutes at 200° C. and 50 rpm.

The mixture is then compressed at 180° C. for 6 minutes to 2 mm sheets from which discs of 26 mm diameter are punched as test specimens.

The Yellowness Index of these test specimens is then determined (photometer: Datacolor 3890, aperture 27, without UV, without gloss, standard light C., 2° detector). The results are reported in Table 3.

TABLE 3

| Polymer of | Yellowness Index |
|---|---|
| Example 12 | 8.3 |
| Example 13 | 8.2 |

EXAMPLE 14

Stabilisation of Polypropylene 100 parts of ®Profax 6501 (polypropylene sold by Himont, USA; MF[230° C./2.16 kg] 3.2), 0.05% of the phenol of Example 1 and 0.05% of calcium stearate are repeatedly extruded at a maximum temperature of 280° C. and 40 rpm.

After each extrusion a portion of the mixture is taken and compressed to 2 mm sheets. The compression conditions are given in Table 4. Discs of 26 mm diameter are punched from these sheets as test specimens for determining the Yellowness Index (photometer: Datacolor 3890, aperture 27, without UV, without gloss, standard light C., 2° detector). The results are reported in Table 4.

TABLE 4

| Compression °C./min | Yellowness Index after extrusion | | |
|---|---|---|---|
| | 1 | 3 | 5 |
| 260/6 | 3.5 | 3.9 | 4.3 |
| 300/6 | 3.4 | 3.6 | 4.2 |

EXAMPLE 15

Stabilisation of X-SBR Latex (Carboxylated SBR Latex)

0.25 part by weight of each of the novel compounds listed in Table 5 is dissolved in a small amount of methanol and the solution is stirred into 100 parts by weight of X-SBR latex (styrene-butadiene copolymer). An exactly defined mount of latex is filled into petri dishes and dried in a drying cabinet at 80° C. to give transparent films having a layer thickness of c. 0.2 mm. A sample without stabilisers is prepared for comparison purposes. The effectiveness of the additives incorporated in the latex is tested by heat ageing in a recirculating air oven at 150° C. The discolouration of the specimens is determined according to the Yellowness Index of ASTM D 1925-70. Higher values denote more intensive yellowing.

TABLE 5

| Stabiliser of Example | Yellowness Index after ageing at 150° C. after | | |
|---|---|---|---|
| | 2 | 4 | 6 hours |
| — | 93 | * | * |
| 1 | 32 | 58 | 71 |
| 2 | 30 | 56 | 71 |
| 3 | 32 | 56 | 70 |
| 4 | 36 | 56 | 74 |
| 5 | 37 | 61 | 75 |
| 7 | 33 | 59 | 74 |
| 8 | 38 | 62 | 77 |
| 9 | 33 | 58 | 74 |
| 10 | 33 | 59 | 70 |

*black, not measurable

EXAMPLE 16

Stabilisation of Polyol 0.3% of the stabiliser to be tested are stirred in 20 g of Lupranol ®2045 (unstabilised polyol) until a clear, colourless solution is obtained. Then 1000 mg of each of these solutions are subjected to an oxidation test in a Rancimat ® oxidiser supplied by Metrohm. Passing oxygen over polyol at elevated temperature causes the onset of an oxidation reaction. The reaction can be easily detected, as the oxidation products formed are readily volatile and, in addition, acidic, so that after collection in water they increase the conductivity (measured in $\mu s/cm$) of the solution. Addition of stabilisers prevents this oxidation reaction quantitatively up to complete consumption of the stabiliser. If the conductivity is measured as a function of the time, then the start of oxidation is represented by the trace of the curve (linear increase). The time taken from the start of the test to the rise in the curve is a benchmark for the effectiveness of the stabiliser. The results are reported in Table 6.

TABLE 6

| Stabiliser compound of Example | Minutes taken to reach a conductivity of 25 $\mu S/cm$ at 150° C. in $O_2$ |
|---|---|
| reference* | 37 |
| 3 | 40 |
| 4 | 44 |
| 6 | 40 |

*2,6-di-tert-butyl-p-cresol

EXAMPLE 17

Deposit and Oxidation Panel Test (DOPT)

The Deposit and Oxidation Panel Test (DOPT) is a variant of the test method for engine oils, especially for diesel engine oils, which has been described by G. Abellaneda et al IIIè Symposium CEC, 1989, 61, New Cavendish Street, London WIM8AR, England. It is used for testing the suitability of the oils containing stabiliser for preventing deposits on pistons.

In a humid atmosphere which is enriched with 260 ppm of $NO_2$ and 26 ppm of $SO_2$, test oil is dripped on to a heated metal plate (panel). The test time is 20 seconds, the panel temperature 260° C., and the oil flow 1 ml/minute. After the test, the deposits on the panel on to which the oil drips are measured by weighing. A second assessment is made visually. In the visual assessment, the lower values correspond to the best results. The lubricant oil is a commercially available CD oil which is diluted with STANCO 150 base oil. The stabilisers are blended with this oil in an amount of 0.6% by weight, based on the oil, and subjected to the DOPT test. The results are reported in Table 7.

TABLE 7

| Stabiliser of Example | Deposits on the panel | |
|---|---|---|
| | weight [mg] | visual |
| without | 72.0 | 14 |
| 1 | 22.5 | 6 |

What is claimed is:

1. A compound of formula I

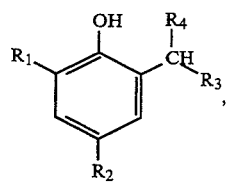

(I)

wherein
 $R_1$ is $C_1$-$C_4$n-alkyl, isopropyl, s-butyl, cyclopentyl, cyclohexyl or α-methylbenzyl,
 $R_2$ is $C_4$-$C_{18}$tert-alkyl or α,α-dimethylbenzyl,
 $R_3$ is $C_1$-$C_{28}$alkyl, and
 $R_4$ is methyl or ethyl, with the proviso that the —$CHR_3R_4$ group contains at least 4 carbon atoms.

2. A compound of formula I according to claim 1, wherein $R_1$ is methyl, ethyl, s-butyl or cyclohexyl.

3. A compound of formula I according to claim 1, wherein $R_1$ is methyl or s-butyl, $R_2$ is $C_4$-$C_8$tert-alkyl and $R_3$ is $C_1$-$C_{22}$n-alkyl.

4. A compound of formula I according to claim 1, wherein $R_1$ is methyl.

5. A compound of formula I according to claim 1, wherein $R_4$ is methyl.

6. A compound of formula I according to claim 1, wherein $R_3$ is $C_8$–$C_{22}$n-alkyl.

7. A compound of formula I according to claim 1, wherein $R_2$ is $C_4$–$C_8$tert-alkyl.

8. A compound of formula I according to claim 1, wherein $R_2$ is tert-butyl.

9. A mixture of compounds of formula I according to claim 1, wherein $R_4$ is methyl, with those wherein $R_4$ is ethyl.

10. A mixture according to claim 9, wherein the ratio of the compounds of formula I, wherein $R_4$ is methyl, to those wherein $R_4$ is ethyl, is 99:1 to 90:10.

11. A mixture according to claim 9, wherein the chain length of $R_3$ in a compound of formula I, wherein $R_4$ is methyl, is greater by one than in a compound of formula I, wherein $R_4$ is ethyl.

12. A product obtainable by reacting a phenol of formula

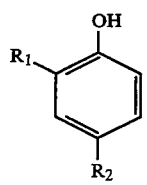

with an α-olefin of formula $CH_2\!=\!CH\!-\!R_3$, wherein $R_1$, $R_2$ and $R_3$ are defined as in claim 1.

13. A composition comprising (a) an organic material which is susceptible to degradation induced by oxidation heat or actinic light, and (b) at least one compound of formula I or mixture thereof.

14. A composition according to claim 13, wherein component (a) is selected from the group consisting of polystyrene, substituted polystyrene, a co- or terpolymer of polystyrene or substituted polystyrene, a polycarbonate, a polyester carbonate, a polyurethane, a polyamide homopolymer, a copolyamide, a polyacetal, a polyphenylene oxide, a polyolefin, a mineral oil, a vegetable or animal oil and a fat.

15. A composition according to claim 13, wherein component (a) is selected from the group consisting of polystyrene, a substituted polystyrene, a co- or terpolymer of styrene or substituted styrene.

16. A composition according to claim 13, wherein component (a) is selected from the group consisting of impact-resistant polystyrene, a styrene-acrylonitrile copolymer, an acrylonitrile-butadiene-styrene terpolyrmer, and a methyl methacrylate-butadine-styrene graft copolymer.

17. A composition according to claim 13, wherein component (a) is an acrylonitrile-butadiene-styrene terpolymer.

18. A composition according to claim 13, wherein component (a) is selected from the group consisting of a polycarbonate, a polyester carbonate, a polyurethane, a polyamide homopolymer, a copolyamide, a polyacetal and a polyphenylene oxide.

19. A composition according to claim 13, wherein component (a) is a polyolefin.

20. A process for stabilising organic material which is susceptible to degradation induced by heat, oxidation or actinic light, which comprises incorporating in or applying to said material at least one compound of formula I or mixtures thereof.

21. A composition comprising (a) an organic material which is susceptible to degradation induced by oxidation heat or actinic light, and (b) at least one product according to claim 12.

22. A composition according to claim 21, wherein component (a) is selected from the group consisting of polystyrene, substituted polystyrene, a co- or terpolymer of polystyrene or substituted polystyrene, a polycarbonate, a polyester carbonate, a polyurethane, a polyamide homopolymer, a copolyamide, a polyacetal, a polyphenylene oxide, a polyolefin, a mineral oil, a vegetable or animal oil and a fat.

23. A composition according to claim 21, wherein component (a) is selected from the group consisting of polystyrene, a substituted polystyrene, a co- or terpolymer of styrene or substituted styrene.

24. A composition according to claim 21, wherein component (a) is selected from the group consisting of impact-resistant polystyrene, a styrene-acrylonitrile copolymer, an acrylonitrile-butadiene-styrene terpolymer, and a methyl methacrylate-butadiene-styrene graft copolymer.

25. A composition according to claim 21, wherein component (a) is an acrylonitrile-butadiene-styrene terpolymer.

26. A composition according to claim 21, wherein component (a) is selected from the group consisting of a polycarbonate, a polyester carbonate, a polyurethane, a polyamide homopolymer, a copolyamide, a polyacetal and a polyphenylene oxide.

27. A composition according to claim 21, wherein component (a) is a polyolefin.

* * * * *

UNITED STATES PATENT AND TRADEMARK OFFICE
CERTIFICATE OF CORRECTION

PATENT NO. : 5,356,976
DATED : OCTOBER 18, 1994
INVENTOR(S) : PAUL DUBS, ET AL.

It is certified that error appears in the above-identified patent and that said Letters Patent is hereby corrected as shown below:

Column 19, line 33, should read -- (b) at least one compound of formula I , according to claim 1, or mixture thereof. --

Column 20, line 4, should read -- at least one compound of formula I , according to claim1, or mixture thereof. --

Signed and Sealed this

Second Day of May, 1995

Attest:

BRUCE LEHMAN

*Attesting Officer*      *Commissioner of Patents and Trademarks*